United States Patent [19]

Gitel et al.

[11] Patent Number: 4,883,751

[45] Date of Patent: Nov. 28, 1989

[54] SPECIFIC IMMUNOASSAY FOR HEPARIN

[75] Inventors: Sanford N. Gitel, Elizabeth, N.J.; Stanford Wessler, Rye, N.Y.

[73] Assignee: New York University, New York, N.Y.

[21] Appl. No.: 868,122

[22] Filed: May 28, 1986

[51] Int. Cl.$^4$ .................. G01N 33/543; G01N 53/00
[52] U.S. Cl. .................... 435/7; 435/28/810; 436/501,518; 436/547; 436/808; 436/815; 530/387
[58] Field of Search .............. 435/7, 28, 810, 13; 436/501, 518, 547, 808, 809, 815; 427/2; 422/99; 530/387; 528/422

[56] References Cited

U.S. PATENT DOCUMENTS

| | | | |
|---|---|---|---|
| 4,134,792 | 1/1979 | Boguslaski et al. | 435/4 |
| 4,202,872 | 5/1980 | Collen | 436/520 |
| 4,543,335 | 9/1985 | Sommer et al. | 435/13 |

OTHER PUBLICATIONS

H. Bessos, *Thrombosis Research*, 35, 267–278, 1984.
J. Dawes et al., *Thrombosis Research*, 27, 387–396, 1982.
J. Dawes et al., *Chem. Abs.*, 104, 132K, 1986.
S. N. Gitel et al., *Blood*, 65, 902–911, 1985.
W. D. Stansfield, *Serology and Immunology*, MacMillan Publishing, Co., Inc., New York, 1981, pp. 269–271.
Dawes et al., *Thrombosis and Haemostasis*, 54, 630–634, 1985.
*The Merck Index*, 10th Ed., Entry No. 4578, pp. 677–678, 1983.

*Primary Examiner*—Esther M. Kepplinger
*Assistant Examiner*—David A. Saunders
*Attorney, Agent, or Firm*—Darby & Darby

[57] ABSTRACT

Disclosed herein are assays for measuring the amount of heparin present in a biological sample. The assays use a positively charged polycarbodiimide heparin-inhibitor compound and antibodies which recognize heparin when bound to the carbodiimide inhibitor but do not react with free heparin.

21 Claims, 1 Drawing Sheet

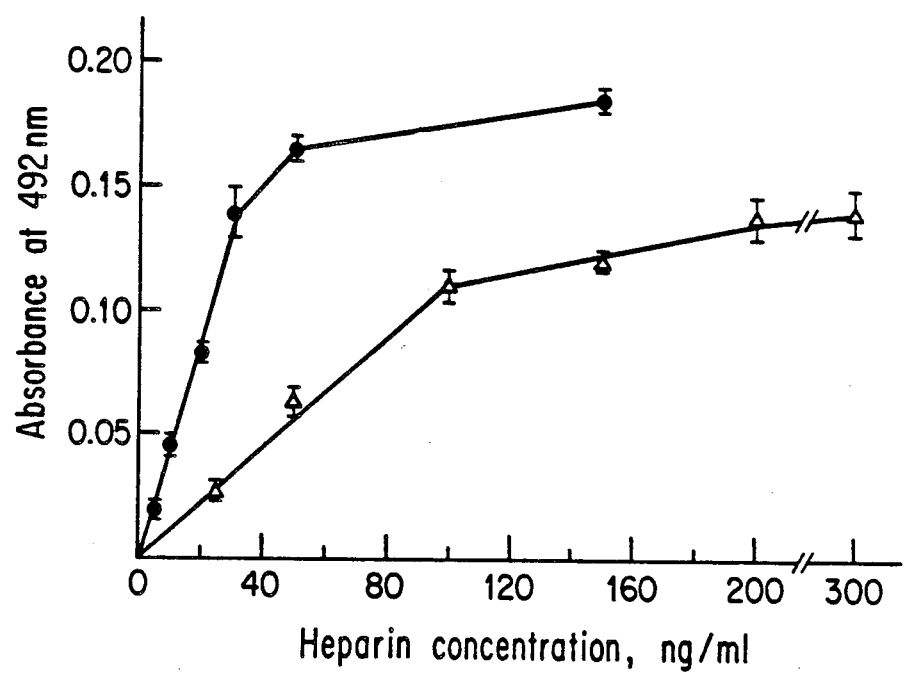

SPECIFIC IMMUNOASSAY FOR HEPARIN

FIELD OF THE INVENTION

This invention relates to a specific immunoassay for heparin and novel reagents used therein.

BACKGROUND OF THE INVENTION

Heparins are a heterogeneous group of mucopolysaccharides consisting of alternating residues of D-glucosamine and D-glucuronic acid joined by 1-4 linkages. Heparins can be found in various mammalian tissues, especially in the liver, the lung, as well as in mast cells. In the plasma, heparin is known to inhibit coagulation and also to accelerate the removal of triglycerides from the blood.

Heparins are commonly used anticoagulant drugs. The best understood action of heparin is in the inactivation of thrombin, which is thus prevented from acting on fibrinogen. Blood contains a naturally occurring inhibitor of thrombin, termed antithrombin III, which combines with the thrombin molecule and inactivates it. Heparin binds to antithrombin III, thereby markedly accelerating the reaction between thrombin and antithrombin III, and thus causing the inactivation of thrombin.

Heparin also acts earlier in the coagulation sequence by accelerating the combination of antithrombin III with other blood coagulation factors, in particular factors IXa, Xa, XIa and XIIa. Consequently, the results of all coagulation tests will be affected if heparin is present in the plasma or serum tested.

Specific methods for measuring heparin concentrations in plasma and other biological fluids are needed both to evaluate the relation between heparin concentration and its biological effects and for pharmacological studies.

Several types of heparin assays are currently available. Chemical methods, such as the uronic acid carbazole reaction, can be used to detect many different heparins but are relatively insensitive and frequently require a purified sample in order to yield quantitative results. Jacques, et al. (*Analyt. Biochem.* 52: 219-233, 1973) disclosed an assay for the identification and quantitation of heparins which comprised microelectrophoresis of samples on agarose gels coupled with staining with toluidine blue solutions. A linear relationship was observed between absorbance and heparin concentration applied so that the total optical density of spots could be used to estimate the heparin concentration. Although this assay permitted the measurement of heparin in complex mixtures, it was too insensitive and too cumbersome for routine use.

Biological assays for heparin are based on the overall anticoagulant activity of heparin, or on more specific properties such as the inactivation of thrombin or coagulation factors. Yin, et al., (*J. Lab. Clin. Med.* 81: 298-310, 1973) described a quantitative assay for heparin which was said to detect as little as 0.01 units of heparin activity (corresponding to 0.1 micrograms of heparin). The assay was based upon the accelerating effect of heparin on the neutralization of activated factor X by its plasma inhibitor, antithrombin III.

Teien, A. N. and Lie, M. (*Thromb. Res.* 7: 777-788, 1975) evaluated five clotting methods for the determination of heparin activity in plasma including the activated partial thromboplastin time (APTT); the calcium thrombin time; the method of Yin, et al., above; titration with Polybrene; and the method of Denson and Bonnar (*Thromb. Diath. Haemorrh.*, 30: 4711, 1973), the latter being a modification of Yin, et al. (op. cit.).

Teien, et al. reported considerable variation between the values obtained with the different biological assays. This is not surprising because each of these biological assays depends upon a different property of the heparin molecule. The clotting assays investigated by Teien, et al. are global tests in that they measure the resultant activity arising from a balance between activators and inhibitors of the coagulation system. These assays are useful in monitoring the biological activities of the heparin molecule. However, heparin treatment itself reduces the level of antithrombin III. Moreover, in the course of a disease, the heparin sensitivity in the blood may change. In addition, heparin antagonists in the blood, such as platelet factor 4, may increase. Hence, for the objective determination of total heparin levels (independent of biological function), these assays are of limited usefulness.

In an attempt to overcome the problems inherent in biological assays such as the one described above, Dawes and Pepper (*Thromb. Res.* 27: 387-396, 1982), described a competitive binding assay for exogenous and endogenous heparins. In this assay, heparin is said to compete with radioactively labeled heparin for binding to protamine-Sepharose. Although this assay is said to be quite sensitive (the article reports detection of heparin at concentrations as low as 10 ng per ml), it requires an incubation period of at least 16 hours just for binding. Moreover, time is required to predigest the biological fluid to be tested in order to remove interfering substances and yield an assayable sample. The long duration of this assay and the need for predigestion make it unsuitable for clinical use and cumbersome for use in determining heparin levels in nonclinical applications. Furthermore, this assay is not specific because it also recognizes a variety of other sulfated polysaccharides, such as heparan sulfate.

Bessos, H. (*Thromb. Res.* 35: 267-278, 1984) described a process for degrading heparin and heparan sulfate with various chemical methods, and assaying the degradation products with the competitive binding assay of Dawes and Pepper. Treatment with nitrous acid was found to degrade heparin faster and to a greater extent than heparan sulfate. Assay of the degradation products could be used to correct the last of specificity of the competitive assay of Dawes and Pepper. However, this modification of the Dawes and Pepper assay renders the assay procedure even longer and more complex, and thus unsuitable for routine laboratory use.

Therefore, there is a need in the art to provide a system to detect heparin which is faster, more specific, sensitive and independent of any biological functions of the molecule. The utility of such an assay is manifold. For example, the assay could be used together with activity assays to determine the amount of heparin required to obtain a given antithrombotic level, thereby providing the clinician with a more precise estimate of the risk of raising or lowering the dosage of heparin employed. It also could be used as a biological probe for the presence of heparin in various cells and tissues and in solid matrices such as endothelial or heparinized synthetic surfaces, topics of increasing importance to the fields of atherosclerosis and non-thrombogenic surfaces, including artificial hearts and heart valves. Finally, there is a need for an assay that distinguishes between heparin and related glycosaminoglycans.

The present inventors have devised a rapid, sensitive and specific assay for heparin in biological fluids. As used in this application, biological fluids include but are not limited to plasma, urine, cell suspensions, tissue extracts and other bodily and physiological fluids which may contain heparin. This assay and the reagents employed herein are also useful during the commercial scale isolation and purification of heparin for pharmacological use, and as a probe for the presence of heparin in tissues.

OBJECTS OF THE INVENTION

The present invention has several objects including, but not limited to, the following:

to provide an accurate, sensitive and specific method for measuring the concentration of heparin in a biological fluid;

to provide a new assay for heparin which overcomes the above-mentioned drawbacks of conventional biological and/or chemical methods;

to provide a sensitive, reproducible binding assay for heparin which does not display cross-reactivity with other related polysaccharides and proteoglycans and can be used in routine diagnostic and patient management laboratory tests and investigations;

to provide a positively charged polycarbodiimide compound useful as an inhibitor of or to detect heparin;

to provide an anti-heparin antibody that binds to heparin in turn bound to said polycarbodiimide inhibitor; and to provide a method for the purification of heparin using the polycarbodiimide inhibitor.

These and other objects of the present invention will be apparent to those skilled in the art in light of the present description, accompanying claims and appended drawings.

BRIEF DESCRIPTION OF THE DRAWING

FIG. 1 is a plot of absorbance at 492 nm against heparin concentration in a sample.

SUMMARY OF THE INVENTION

One aspect of the present invention is directed to a method for determining the concentration of heparin present in a biological fluid comprising binding said heparin to a heparin inhibitor to form a detectable heparin/inhibitor complex;

measuring the amount of the thus formed complex and deriving the concentration of heparin by reference to said amount.

Another aspect of the invention is directed to an assay for measuring the amount of heparin present in a biological fluid comprising the steps of:

incubating a sample of said fluid in the presence of an immobilized methylated polycarbodiimide heparin inhibitor, thereby causing the heparin contained in said sample to bind to said inhibitor and form an immobilized heparin-inhibitor complex;

discarding the unbound sample;

incubating the heparin-inhibitor complex with a first antibody, said first antibody being an anti-heparin antibody immunochemically reactive with said heparin-inhibitor complex, thereby causing said first antibody to bind to said heparin-inhibitor complex and form an immobilized (heparin-inhibitor) anti-heparin complex;

discarding unbound first antibody;

incubating said heparin-inhibitor-anti-heparin complex with a second antibody immunochemically reactive with said first antibody, said second antibody being capable of being quantitatively detected, thereby forming an immobilized heparin-inhibitor-anti-heparin-(second antibody) complex;

discarding unbound second antibody; and determining the amount of said immobilized second antibody.

Yet another aspect of the present invention is directed to a positively charged (for example, alkylated and, preferably, methylated) polymer of 1-ethyl-3-(3-dimethylaminopropyl)carbodiimide, useful as a heparin inhibitor. The polymer of the present invention has an average molecular weight of between about 7,000 and about 10,000 daltons and is synthesized by neutralization of 1-ethyl-3-(3-dimethylaminopropyl)carbodiimide hydrochloride, polymerization and methylation. A postulated structure for the methylated polymer of the present invention is:

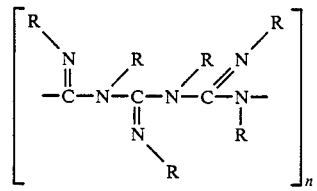

wherein R is selected from the group consisting of ethyl, dimethylaminopropyl, and trimethylaminopropyl.

A further aspect of the present invention is directed to a method for the purification of heparin comprising the steps of:

loading a mixture comprising impure heparin and an ionic buffer to a chromatography column comprising an immobilized, polymeric heparin inhibitor equilibrated with the same buffer;

washing the column with a buffer with increased ionic strength; and eluting said column with a buffer comprising 1M sodium chloride ions.

DETAILED DESCRIPTION OF THE INVENTION

The present invention is described below by reference to preferred embodiments. It will be understood, however, that the scope of this invention will not be limited to these embodiments.

The present invention is directed to a rapid, sensitive and specific assay for measuring heparin in a biological fluid. This assay can be performed directly on a biological sample without pretreatment. In addition, there are no limitations on the samples that can be used in that the assay is highly selective and detects no other cross-reactive compounds. This not only saves valuable time, but it also avoids excessive handling of the sample, which might decrease the accuracy of the assay. Biological samples include but are not limited to whole blood, blood serum, plasma, urine, cerebrospinal fluid, tears, culture media, cell extracts, etc.

The present assay typically yields results in less than fifty percent of the time required for the Dawes and Pepper assay, for example in eight hours or less. The assay can be performed in 4–5 hours if it is known that the sample contains at least 100 ng/ml of heparin and by increasing the concentration of the anti-heparin antibody employed (see below. This makes the present assay suitable for use (and advantageous) whenever accurate measurements of total heparin concentration are required. It is also possible to employ this assay clinically as an adjunct in the management of surgery patients and in other clinical applications where precision is needed.

The present assay is specific in that it recognizes no other glycosaminoglycans (such as heparan sulfate) or other heparin-related substances. It is also extremely sensitive in that it can measure concentrations of heparin at least as low as about 5-10 ng/ml.

Finally, the present assay is not a biological assay and thus it does not have the disadvantages of the clotting assays for the measurement of heparin. In one preferred embodiment, the present assay is a variant of an Enzyme-Linked Immunosorbent Assay (ELISA). In another preferred embodiment, the present assay is a variant of a radioimmunoassay (RIA).

The present inventors have discovered and synthesized novel methylated polymers believed to correspond to the general formula:

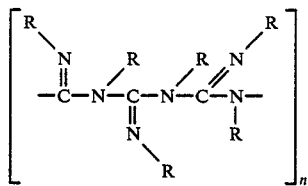

wherein R is selected from the group consisting of: ethyl, dimethylaminopropyl, and trimethylaminopropyl. This polymer results from the methylation of polymers of one or both of the monomers:

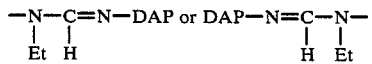

wherein DAP is dimethylaminopropyl and Et is ethyl.

These compounds are effective heparin inhibitors and bind heparin with high affinity and specificity due to ionic interactions.

The polymers of the present invention can be synthesized conveniently and inexpensively as follows:

(1) Neutralization of 1-ethyl-3-(3-dimethylaminopropyl)carbodiimide hydrochloride with sodium carbonate.

(2) Polymerization preferably at room temperature (22° C.) for at least about two days (and preferably for about two weeks) or at elevated temperatures (100° C.) for about 2-5 hours.

(3) Methylation with methyl iodide overnight at 22° C. using 2 moles methyl iodide per mole of monomer.

The details of this synthesis are provided in Example 3 below. Methylation is a preferred method for conferring a postive change on the polymer.

The heparin inhibitors of the present invention can be immobilized by binding onto a solid substrate, such as a microtiter plate (Costar, Cambridge, MA) or to Sepharose 4B beads for the purification of heparin (Paper Ex. 1 below).

The inhibitor is bound to the substrate microtiter plate well by incubating for about 1 to about 2 (and preferably 1.75) hours at room temperature. Unbound inhibitor is washed, preferably with 0.14M Tris-buffered saline (pH 7.5) can be stored for up to about six weeks at 4° C. under normal saline or, preferably, may be stored dry until use.

In a a preferred embodiment, prior to use, the inhibitor-bearing substrate is washed and a solution of sample in buffer is added. The wells are incubated for at least about 5 (and preferably about 5-7) hours and unbound sample is washed with buffer. Shorter incubation times can be employed when assaying samples containing more than 25 ng/ml of heparin. Shorter incubation times are also possible if lower accuracy of measurement can be tolerated.

A preparation (e.g. in Tween-containing PBS) containing a first antibody raised against heparin (See Example 4 below) and capable of recognizing heparin bound to the inhibitor is introduced into each well and incubated at room temperature for a period of time ranging from about one to three hours, with two hours being preferred.

The antibody solution is removed by washing and a second anti-IgG-antibody preparation is introduced into the wells. The second antibody recognizes and binds to the anti-heparin antibody already bound to the immobilized heparin-inhibitor complex. The second antibody can be detected; for example, it can be conjugated with a revealing substance such as an enzyme that leads to activation of a chromophore compound, a fluorescent substance, such as fluorescein, or it can be labelled with a radioactive isotope such as $^{125}$I. Further revealing substances that can be used in conjunction with peroxidase as a revealing agent include but are not limited to the following: 2,2'-azino-di(3-ethylbenzthiazoline sulfonic acid)-6 ammonium salts, orthodianisidine, 5-aminosalicylic acid, 3,3'-dimethyloxybenzidine and para-cresol. In addition other combinations exist, such as anti-IgG-alkaline phosphatase/paranitrophenyl phosphate, as is well-known in the art.

The amount of revealing (second) antibody can then be measured and the corresponding heparin concentration can be determined by reference to standard measurements, as is well known in the art.

In an alternative embodiment, the methylated carbodiimide inhibitor (0 to 400 ng/ml final concentration) and anti-heparin antibodies (at a concentration selected to yield half-maximal binding heparin bound to inhibitor in turn bound to microtiter plate i.e. 50-100 ng/ml) are mixed with a heparin-containing sample. 50 microliter aliquots of the mixture are added to a well of a microtiter plate containing immobilized heparin-inhibitor complex and allowed to react for 2-3, preferably 2.5 hours, at room temperature. The reaction mixtures are removed and the washing and detection steps are identical to those of the preferred embodiment.

Using this technique, heparin can be quantitated by its ability to inhibit the binding of the anti-heparin antibodies to wells coated with heparin bound to the inhibitor.

The anti-heparin antibody can be prepared following the procedures in Example 4 below.

The present invention is described further below in specific examples which are intended to illustrate it without limiting its scope.

EXAMPLE 1

Preparation of the Assay

Fifty microliters of the methylated carbodiimide heparin inhibitor in 0.14M Tris buffered normal saline (prepared in accordance with Example 4) at a concentration of 1.0–1.25 micrograms/ml are added to the wells of a microtiter plate and incubated for 1.75 hours at room temperature. The wells are extensively washed with 0.14M Tris-buffered normal saline (pH 7.5) and stored for up to six weeks at 4° C. preferably dry or with 100 microliters of normal saline in each well. Before use, the wells are washed twice with 200 microliters of 0.3M NaCl, 0.03M phosphate (pH 7.2), and 0.05% Tween 20 (Tween buffer).

EXAMPLE 2

Performance of the Assay

Fifty or 100 microliters of a heparin-containing sample in Tween buffer (or in plasma) are added to each well and incubated overnight at 4° C. or preferably for five hours at room temperature. The samples are removed and the wells washed five times with 200 microliters of Tween buffer. Fifty microliters of a dilute solution of anti-heparin antibody (see Example 5 below) in Tween buffer are placed in each well and incubated at room temperature for about two hours.

The antibody content of the solution depends on the activity of the anti-heparin antibody, but generally will range between about 100 and about 200 ng/ml when using an IgG-fractionated antibody preparation. In order to decrease the time of incubation at this stage, concentrations of about 1 microgram/ml are preferred.

The antibody solution is removed and the wells are washed five times with 200 microliters of Tween buffer. Fifty microliters of goat anti-rabbit IgG peroxidase in Tween buffer are placed in each well and incubated at room temperature for one hour. The antibody is then removed and the wells washed four times with 200 microliters of Tween buffer and twice the 200 microliters of 0.1M phosphate/citrate buffer, pH 5.0 (prepared by mixing 60.75 ml 0.1M citric acid, 128.75 ml of dibasic sodium phosphate and water to 250 ml). One hundred microliters of a solution containing hydrogen peroxide (0.015%) and ortho-phenylenediamine (0.05% w/v) (Sigma Chemical Co., St. Louis, MO) in the phosphate/citrate buffer are placed in each well and the color allowed to develop for 10–20 minutes.

The reaction is stopped by an addition of 50 microliters of 4N sulfuric acid. 100 microliters of this mixture is added to 0.9 ml of water and the optical density at 492 nm is determined. Alternatively, the optical density can be read directly on a spectrophotometer specifically adapted to read microtiter plates.

EXAMPLE 3

Preparation of Methylated Polymeric Ethyl Dimethylaminopropyl Carbodiimide Heparin Inhibitor 1-ethyl-3-(3-dimethylaminopropyl)carbodiimide hydrochloride (available commercially from Sigma Chemical Co.) was neutralized in a 10% solution of sodium carbonate. The monomer carbodiimide was extracted with methylene chloride, dried over solid potassium hydroxide, and isolated by removing the solvent at reduced pressure. The isolated free amine was allowed to polymerize by storing in the dark, preferably for 1–2 weeks or by heating at 100° C. for several hours. Two grams of the white, semi-solid reaction mixture were washed with excess deionized water in order to remove any unpolymerized carbodiimide. The resulting polymer, which is relatively insoluble in aqueous media, was isolated by filtration and dried at reduced pressure to yield 1 gram of a white solid.

500 mg of the polymer, in 100 ml of anhydrous diethyl ether (Fisher Chemical Co., Fairfield, NJ) was mixed with 500 mg methyl iodide (Fisher Chemical Co.), and the reaction mixture was stirred overnight at room temperature. The resulting white precipitate was isolated by filtration, washed with 500 ml of anhydrous diethyl ether and dried in vacuo to yield 400 mg of a white solid. This white solid is the methylated carbodiimide polymeric inhibitor. It is relatively water soluble and has a mean molecular weight of 8,000 as determined by gel chromatography on Sephadex G-100 and G-50 (Pharmacia, Piscataway, NJ) and by partial retention on an Amicon UM-10 membrane. It inhibited heparin anticoagulant activity at about a 1:1 weight-to-weight ratio.

EXAMPLE 4

Preparation of Antibodies

Because heparin is a naturally occurring mucopolysaccharide, simple immunization procedures do not elicit substantial anti-heparin binding activity. That this is indeed the case is suggested by the nearly total lack of reports of antigenic responses to either bovine or porcine-derived heparins employed as anticoagulants in man.

A technique which has been employed to elicit antibodies to non-immunogenic substances is to use their precipitates with methylated bovine serum albumin (BSA) as the immunogen. Using this procedure, antibodies with specificities directed against DNA fragments, polyribonucleotides and poly-D-glutamic acid (all poor immunogens) have been obtained. This technique was used to obtain the anti-heparin antibodies of the present invention.

Anti-heparin antibodies, which recognize carbodiimide-modified heparin, have been described (Gitel, S.N., et al., *Blood* 65: 902–911, 1985). These were generated by immunizing rabbits with protein-heparin complexes obtained by reactions with water-soluble (monomeric) carbodiimides. However, both the complexes used to immunize the rabbits and the antibodies produced are different from those of the present invention. The antibodies of the present invention are more effective (i.e., have higher heparin neutralizing titers) and were generated against heparin-methylated bovine serum albumin complexes, not carbodiimide-modified heparin, as in Gitel, et al. (op. cit.).

Bovine serum albumin (U.S. Biochemicals, Pittsburgh, PA) was methylated by the well-known method of Sueok, N. and Cheng, T. Y. (*J. Mol. Biol.* 4: 161–172, 1962, incorporated by reference). Methylated BSA-heparin precipitates were obtained by mixing equal volumes of methylated BSA (5 mg/ml) with heparin (1 mg/ml, Grade I, Sigma Chemical Co.) in deionized water. The resulting precipitate was pelleted, washed with deionized water and dried under reduced pressure at room temperature.

Three different immunization regimens were employed in order to elicit anti-heparin antibodies.

1. Female New Zealand white rabbits were immunized by a single intravenous injection of 2 mg of methylated BSA-heparin precipitate suspended in one ml of 0.14M Tris saline solution. Similar booster immunizations were given 20, 50 and 80 days after the initial injection. Blood samples were obtained four days after each immunization.

2. A second set of rabbits were immunized by the intradermal injection of 200 micrograms of methylated BSA-heparin precipitate in complete Freund's adjuvant and the intravenous injection of 50 micrograms of the precipitate suspended in 200 microliters of a 0.14M NaCl solution on days 1, 4, 8 and 11. After resting for two months, the rabbits were re-immunized as above. Blood samples were obtained four days after the completion of each set of immunizations.

3. A third set of rabbits were immunized by the intradermal injection of 200 micrograms of methylated BSA-heparin precipitate in complete Freund's adjuvant and the intravenous injection of 50 micrograms of precipitate in 200 microliters of a 0.14M Tris saline solution on days 1, 8 and 14. On days 20 and 40, the rabbits received in intravenous injection of 100 micrograms of the precipitate in 200 microliters of a 0.14 Tris saline solution. A booster intravenous injection of 100 micrograms of the precipitate was administered two months after the completion of the initial immunization schedule. Blood samples were obtained four days after injection on day 18.

Blood samples were collected into citrate and plasma was obtained by centrifugation. The plasma was heated at 56° C. for 20 minutes and the resulting precipitate was removed by centrifugation. The IgG fraction was isolated by the well-known ammonium sulfate precipitation procedure. The IgG fraction can be employed for the subsequent heparin assays as above or, a partially purified pool of antibodies can be obtained by affinity chromatography on heparin-Sepharose, as is well-known in the art. These latter antibodies yield a lower background in the heparin assays.

The IgG antibody titers obtained using the above immunization schedules are presented below in Table I.

TABLE I

Anti-heparin Antibody Titer of Immunized Rabbits

| Rabbit | Titer* Preimmune | Post-immune | Immunization Schedule |
|---|---|---|---|
| V6 | 1:20 | 1:100 | #2 |
| V7 | <1:10 | 1:5000 | #2 |
| V8 | <1:10 | 1:5000 | #2 |
| V9 | <1:10 | 1:4000 | #2 |
| V10 | <1:10 | 1:1600 | #3 |
| V11 | <1:10 | 1:2500 | #3 |
| V12 | <1:10 | 1:2500 | #3 |
| V13 | <1:10 | 1:600 | #1 |
| V14 | <1:10 | 1:400 | #1 |
| V15 | <1:10 | 1:5500 | #1 |
| V16 | <1:10 | 1:600 | #1 |

*The titers are dilutions of heated plasma sample required to obtain half of the maximum color generation in the enzyme immunoassay system.

Each immunization schedule gave rise to the production of anti-heparin antibodies, with the highest titer obtained in one rabbit (V15) immunized using schedule #1 (Table I). The anti-heparin antibodies did not precipitate heparin nor inhibit heparin anticoagulant activity. Moreover, these antibodies only recognized heparin bound to the methylated carbodiimide polymer and not soluble heparin. Added solution heparin did not inhibit the binding of the antibody in the immunoassay, but when the methylated carbodiimide polymer was added with heparin, the binding of the antibody was inhibited.

EXAMPLE 5

Measurement of Heparin Content of a Biological Sample

Heparin (Grade I, Sigma Chemical Co.) solutions were diluted in either Tween buffer or human plasma, placed in microtiter wells coated with the methylated polycarbodiimide polymer and allowed to adsorb overnight. The wells were treated with anti-heparin antibody followed by goat-anti-rabbit-IgG peroxidase (Sigma Chemical Co., St. Louis, MO) as described above. Absorbencies at 492 nM that developed after the addition of the hydrogen peroxide/ortho-phenylenediamine solution were measured, and a typical standardization curve for the assay of heparin is presented in FIG. 1.

The assay is sensitive to a minimum of 5 ng/ml of heparin in Tween buffer and 20–25 ng/ml of heparin in plasma (FIG. 1). For commercial heparin, these concentrations, equivalent to $8 \times 10^{-4}$ U/ml and $3.5 \times 10^{-3}$ U/ml respectively, are an order of magnitude lower than that which can be obtained using either specific coagulation or chromogenic substrate-based assays.

A typical immunoassay was performed using known concentrations of seven different heparin samples. The samples were diluted with PBS to give a final concentration of either 10 or 25 ng/ml, and the assay was performed as described above. Two different microplates were used and each contained identical samples, along with dilutions of a standard heparin solution (for the generation of a standardization curve, as in FIG. 1). In addition, each measurement of the absorbance was performed three times. The data are presented below in Table II.

TABLE II

| Heparin Sample | Heparin Concentration ng/ml | | | |
|---|---|---|---|---|
| | Actual | Measured* | Actual | Measured |
| | Plate I | | | |
| SM | 10 | 10.7 ± 0.7 | 25 | 23.7 ± 0.6 |
| SM | 10 | 9.8 ± 0.8 | 25 | 23.0 ± 0.3 |
| SM | 10 | 10.5 ± 1.0 | 25 | 23.0 ± 1.0 |
| 20 | 10 | 9.6 ± 0.2 | 25 | 21.0 ± 0.5 |
| 24 | 10 | 9.6 ± 0.6 | 25 | 20.5 ± 0.2 |
| .5U | 10 | 10.5 ± 0.5 | 25 | 22.1 ± 1.2 |
| .5D | 10 | 10.0 ± 0.6 | 25 | 22.1 ± 0.6 |
| 2U | 10 | 10.0 ± 0.3 | 25 | 22.3 ± 0.4 |
| 2D | 10 | 10.0 ± 0.2 | 25 | 23.0 ± 1.2 |
| | Plate II | | | |
| SM | 10 | 8.8 ± 2.2 | 25 | 23.7 ± 2.0 |
| SM | 10 | 9.5 ± 0.4 | 25 | 20.2 ± 0.4 |
| SM | 10 | 10.0 ± 0.8 | 25 | 21.8 ± 0.4 |
| 20 | 10 | 8.0 ± 0.6 | 25 | 18.2 ± 1.8 |
| 24 | 10 | 8.6 ± 1.2 | 25 | 21.2 ± 3.0 |
| .5U | 10 | 9.2 ± 0.6 | 25 | 21.0 ± 0.4 |
| .5D | 10 | 8.4 ± 1.0 | 25 | 20.7 ± 0.4 |
| 2U | 10 | 9.2 ± 0.6 | 25 | 17.5 ± 1.4 |
| 2D | 10 | 7.2 ± 0.2 | 25 | 21.7 ± 1.6 |

*Each individual measurement is the mean of three independent determinations ± standard deviation.

The above data document the accuracy of this immunoassay. Most samples, at either 10 or 25 ng/ml, could be accurately measured within 10% of their actual values, and there was little variation in the values obtained for the same samples on different microtiter plates (Table II).

The immunoassay was employed using samples containing, other glycosaminoglycans including heparan sulfate (Miles Laboratories, Elkhart, IN), hyaluronic acid (Sigma Chemical Co.), keratan sulfate (Sigma Chemical Co.), dermatan sulfate (Sigma Chemical Co.) and dermatan sulfate (obtained from Dr. Martin Mathews, University of Chicago, Chicago, IL). None of these glycosaminoglycans cross-reacted with heparin in this assay, demonstrating its strict specificity. In addition, none of the above glycosaminoglycans competed with heparin in the immunoassay when added simultaneously.

As can be seen from the above, once the heparin inhibitor is bound to a substrate, hundreds of assays can be performed at the same time, conveniently and inexpensively.

PAPER EXAMPLE 1

Purification of Heparin Using a Methylated Carbodiimide Polymer

The polymeric heparin inhibitor, due to its high affinity and specificity for heparin, can be employed as a reagent for the isolation and purification of heparin. The accomplish this, the polymer will be coupled to a suitable support matrix, such as Sepharose 4B beads (Pharmacia, Piscataway, NJ) by the well-known cyanogen bromide coupling reaction (P. Cuatrecasas, et al. Proc. Nat'l. Acad. Sci. USA 61: 636–643: 1968, incorporated by reference). Heparin-containing samples can be bound with normal Tris saline (0.14M NaCl) and the heparin eluted by the addition of a gradient of 0.5–1M NaCl. It is expected that the majority of heparin will elute when the concentration of NaCl is about 1M. Preferably, the heparin-containing sample can be bound initially in 0.5M NaCl and eluted with a gradient of 0.5–1M NaCl. The latter is preferable since less non-specific binding will occur at the higher salt concentrations.

The invention has been described above by reference to preferred embodiments. It is understood, however, that many additions, deletions and modifications will be apparent to one of ordinary skill in the art in light of the present description without departing from the scope of the invention, as claimed below.

What is claimed is:

1. An assay for measuring the amount of heparin present in a biological fluid comprising the steps of:
   incubating a sample of said fluid in the presence of an immobilized heparin inhibitor, said heparin inhibitor being a positively charged polycarbodiimide compound, thereby causing the heparin contained in said sample to bind to said inhibitor and form an immobilized heparin-inhibitor bimolecular complex;
   incubating the heparin-inhibitor complex with a first antibody, said first antibody being an antibody immunochemically reactive with said heparin-inhibitor complex and not reactive with free heparin, thereby causing said first antibody to bind to said heparin-inhibitor complex and form an immobilized heparin-inhibitor-antibody complex;
   incubating said heparin-inhibitor-antibody complex with a second antibody immunochemically reactive with said first antibody, said second antibody being capable of being quantitatively detected, thereby forming an immobilized heparin-inhibitor-antibody-(second antibody) complex; and
   determining the amount of said immobilized second antibody by reference to the binding of a known amount of said second antibody to a known amount of said heparin-inhibitor-antibody complex.

2. The method of claim 1 wherein said heparin inhibitor comprises a positively charged polymer of 1-ethyl-3-(3-dimethylaminopropyl) carbodiimide.

3. The method of claim 1 wherein any unbound sample is discarded by washing with a buffer comprising 0.3M sodium chloride, 0.03M sodium phosphate, and 0.05% polyoxyethylenesorbital monolaurate, pH 7.2 after formation of said inhibitor-heparin complex.

4. The method of claim 1 wherein said sample is incubated for a period of time ranging between about 5 and about 7 hours.

5. The method of claim 1 wherein said sample is incubated for about 5 hours.

6. The method of claim 1 wherein any unbound first antibody is discarded by washing with a buffer comprising 0.3M sodium chloride, 0.03M phosphate and 0.05% polyoxyethylenesorbital monolaurate, pH 7.2 after formation of said heparin-inhibitor antibody complex.

7. The method of claim 1 wherein said first antibody is a rabbit IgG.

8. The method of claim 1 wherein any unbound second antibody is discarded by washing first with 0.3M NaCl/0.03M phosphate/0.05% polyoxyethylenesorbitan monolaurate, buffer having pH 7.2, and then with 0.3M phosphate/citrate buffer having pH 5.0 after formation of said heparin-inhibitor-antibody-(second antibody) complex.

9. The method of claim 1 wherein said second antibody is a goat anti-rabbit IgG.

10. The method of claim 1 wherein said second antibody is conjugated with a revealing substance selected from the group consisting of peroxidase, fluorescein, alkaline phosphatase, and $^{125}I$.

11. The method of claim 10 wherein said revealing substance is peroxidase, said method further comprising adding hydrogen peroxide and ortho-phenylenediamine to said second antibody complex, waiting for color to develop, and measuring the amount of said bound second antibody by optical means.

12. The method of claim 1 wherein said second antibody is conjugated with a radioactive isotope.

13. The method of claim 12 wherein the amount of said bound second antibody is measured by scintillation counting of radioactivity.

14. A diagnostic kit for assaying the presence of heparin comprising a heparin inhibitor, said heparin inhibitor being a positively charged polycarbodiimide compound; first antibodies recognizing heparin only when said heparin is bound to said heparin inhibitor; antibodies directed against said first antibody and instructions for use of said assay.

15. The kit of claim 14 wherein said heparin inhibitor compound is a methylated polymer of 1-ethyl-3-(3-dimethylaminopropyl)carbodiimide.

16. A solid support containing a methylated polymeric carbodiimide heparin inhibitor bound to (the walls of said microplate) said solid support.

17. An antibody immunochemically reactive with heparin only when said heparin forms a bimolecular complex with a methylated polymeric carbodiimide heparin inhibitor.

18. A method for measuring the concentration of heparin present in a sample comprising complexing heparin in said sample to a heparin inhibitor to form a detectable bimolecular complex between said heparin and said inhibitor, wherein said inhibitor is a positively charged polycarbodiimide; detecting the amount of said complex using antibodies which recognizes said complex and determining the amount of said heparin by reference to a standard, said standard having been obtained by forming complexes between said inhibitor and a known amount of heparin.

19. The method of claim 18 wherein said inhibitor is a positively charged polymer of 1-ethyl-3-(3-dimethylamino-propyl) carbodiimide.

20. A competitive assay for measuring the amount of heparin present in a biological fluid comprising the steps of:

provising an immobilized heparin-inhibitor bimolecular complex of heparin and a heparin inhibitor which is a positively charged polycarbodiimide, exposing said complex to (a) a heparin-containing sample also comprising an excess of said heparin inhibitor in soluble form in an amount more than sufficient to bind to the heparin contained in said sample and (b) an amount of an antibody immunochemically reactive with said heparin-inhibitor complex and not reactive with free heparin, said antibody present in an amount sufficient to bind to a predetermined portion of said immobilized heparin-inhibitor complex, waiting for said heparin in said fluid to react with said soluble heparin inhibitor in said fluid to form a soluble bimolecular heparin-inhibitor complex and for said antibody to bind to said immobilized and said soluble heparin-inhibitor complex, washing off unbound fluid, heparin inhibitor, antibody, and soluble heparin-inhibitor complex, measuring the amount of said bound antibody, and determining the amount of heparin in said fluid by reference to the inhibition by a standard of binding of said antibody to said immobilized heparin-inhibitor complex, said standard having been obtained by forming complexes between the soluble heparin inhibitor and a known concentration of heparin.

21. The method of claim 20 wherein said heparin inhibitor is a positively charged polymer of 1-ethyl-3-(3-dimethylaminopropyl)carbodiimide.

* * * * *